US011998678B2

(12) United States Patent
Grehan et al.

(10) Patent No.: US 11,998,678 B2
(45) Date of Patent: *Jun. 4, 2024

(54) END-OF-DOSE DETECTION IN NEBULIZERS

(71) Applicant: Stamford Devices Limited, Galway (IE)

(72) Inventors: Joseph Grehan, Galway (IE); Michael Casey, County Galway (IE); Shaun Porter, County Galway (IE); Niall Smith, Scotland (GB)

(73) Assignee: Stamford Devices Limited, Galway (IE)

( * ) Notice: Subject to any disclaimer, the term of this patent is extended or adjusted under 35 U.S.C. 154(b) by 207 days.

This patent is subject to a terminal disclaimer.

(21) Appl. No.: 17/194,369

(22) Filed: Mar. 8, 2021

(65) Prior Publication Data
US 2021/0187209 A1 Jun. 24, 2021

Related U.S. Application Data

(63) Continuation of application No. 15/762,387, filed as application No. PCT/EP2016/072541 on Sep. 22, 2016, now Pat. No. 10,967,138.

(30) Foreign Application Priority Data

Sep. 29, 2015 (EP) ..................................... 15187330

(51) Int. Cl.
*A61M 11/00* (2006.01)
*B05B 12/08* (2006.01)
(Continued)

(52) U.S. Cl.
CPC ........... *A61M 11/00* (2013.01); *A61M 11/005* (2013.01); *B05B 15/14* (2018.02);
(Continued)

(58) Field of Classification Search
CPC .............. A61M 11/005; A61M 11/001; A61M 2205/33; A61M 2205/3317; A61M 11/00;
(Continued)

(56) References Cited

U.S. PATENT DOCUMENTS

2006/0102172 A1* 5/2006 Feiner ................. A61M 15/008
128/200.14
2011/0030678 A1* 2/2011 Power ................. A61M 13/003
128/200.14
(Continued)

FOREIGN PATENT DOCUMENTS

WO WO 93/09881 A1 5/1993
WO WO 2011/018777 A1 2/2011
WO WO 2015/010809 A1 1/2015

*Primary Examiner* — Elliot S Ruddie
(74) *Attorney, Agent, or Firm* — Bookoff McAndrews, PLLC

(57) ABSTRACT

A digital processor of a nebulizer controller controls and monitors drive current (I) applied to an aperture plate. The drive current is detected as a series of discrete values at each of multiple measuring points, each having a particular drive frequency The processor in real time calculates a slope or rate of change of drive current with frequency and additionally determines a minimum value for drive current leading up to the peak value. The processor uses both the value of the minimum drive current during the scan and also the maximum slope value to achieve reliable prediction of end of dose, when the aperture plate becomes dry.

14 Claims, 6 Drawing Sheets

(51) Int. Cl.
  *B05B 15/14* (2018.01)
  *B05B 17/00* (2006.01)
  *B05B 17/06* (2006.01)
  *B06B 1/02* (2006.01)

(52) U.S. Cl.
  CPC ...... *B05B 17/0646* (2013.01); *B05B 17/0669* (2013.01); *B06B 1/0253* (2013.01); *A61M 2205/3317* (2013.01); *A61M 2205/3386* (2013.01); *A61M 2205/50* (2013.01); *A61M 2205/583* (2013.01); *B05B 12/081* (2013.01); *B06B 2201/77* (2013.01)

(58) Field of Classification Search
  CPC ........ A61M 2205/50; A61M 2205/583; A61M 2205/3386; G16H 20/10; G16H 20/13; B05B 15/14; B05B 17/0646; B05B 17/0669; B05B 12/004; B05B 12/081; G01N 29/22; G01N 29/42; G06F 19/3456; B06B 1/0253; B06B 2201/77
  See application file for complete search history.

(56) References Cited

U.S. PATENT DOCUMENTS

2015/0320944 A1* 11/2015 Grehan .................. G16H 20/10
                                                                  239/102.2
2016/0310681 A1* 10/2016 Finke ...................... B05B 12/08

* cited by examiner

END-OF-DOSE DETECTION IN NEBULIZERS

CROSS-REFERENCE TO RELATED APPLICATIONS

This application is a continuation of U.S. application Ser. No. 15/762,387, filed Mar. 22, 2018, which is the U.S. national phase entry under 35 U.S.C. § 371 of International Application No. PCT/EP2016/072541, filed on Sep. 22, 2016, which claims priority to European Patent Application No. 15187330.4, filed on Sep. 29, 2015, the contents of all of which are incorporated herein in their entireties.

INTRODUCTION

Field of the Invention

The invention relates to automatic detection of end of dose during operation of a nebulizer.

Prior Art Discussion

It has been known for many years that drive current of a nebuliser plate falling below a threshold, or reaching a minimum is indicative of an aperture plate becoming dry, WO93/09881 (Medix) and WO2011/018777 Aerosurgical).

Our prior PCT specification number WO2015/010809 describes an approach in which slope of a plot of aperture plate drive current vs. drive frequency indicates end of dose (conversion of aperture plate from a wet state to a dry state).

The invention is directed towards improving accuracy of prediction of end of dose.

SUMMARY OF THE INVENTION

According to the invention, there is provided a nebulizer comprising a vibrating aperture plate, a mounting, an actuator, and an aperture plate drive circuit having a controller, wherein the controller is configured to:

- measure aperture plate drive current at each of a plurality of measuring points in a scan, each measuring point having a drive frequency;
- determine a minimum value of the drive current during the scan;
- determine a value for maximum rate of change of drive current during the scan; and to
- use said minimum drive current value in combination with said maximum rate of change value to execute an algorithm to calculate an indicator value for end-of-dose.

In one embodiment, the controller is configured to determine a ratio of said maximum slope value and said minimum value to provide the indicator. In one embodiment, the controller is configured to scale said indicator by a constant value.

In one embodiment, the controller is configured to perform the scan across a frequency range of 128 kHz to 165 kHz.

In one embodiment, the controller is configured to initiate the scan in response to a trigger of possible end of dose. In one embodiment, the trigger is a short scan with a smaller number of measuring points and which detects a change of drive current above a threshold. In one embodiment, the drive current threshold change is above 5 mA, and preferably about 8 mA.

In one embodiment, the actuator is encapsulated.

In one embodiment, a minimum value of drive current which is approximately less than 30% of a minimum value of drive current of a scan for a wet state of the aperture plate is determined as being indicative of end of dose. This may for example contribute to the trigger from the short scan of possible end of dose.

In another aspect, the invention provides a method of operation of a controller of a nebulizer comprising a vibrating aperture plate, a mounting, an actuator, and an aperture plate drive circuit, wherein the method comprises:

- measuring aperture plate drive current at each of a plurality of measuring points in a scan, each measuring point having a drive frequency;
- determining a minimum value of the drive current in said scan;
- determining a value for maximum rate of change of drive current during the scan; and
- using said minimum value in combination with said maximum rate of change value to execute an algorithm to calculate an indicator value for end-of-dose.

In one embodiment, the controller utilizes the ratio of maximum slope value and the minimum parameter value to provide said indicator.

In one embodiment, the controller multiplies said ratio or a value derived from the ratio by a constant value to provide the indicator. In one embodiment, the controller performs the scan across a frequency range of 128 kHz to 165 kHz. Preferably, the controller initiates the scan in response to a trigger of possible end of dose.

In one embodiment, the trigger is a short scan with a smaller number of measuring points and which detects a change of drive current above a threshold. In one embodiment, the drive current threshold change is above 5 mA, and preferably about 8 mA.

In one embodiment, a minimum value of drive current which is approximately less than 30% of a minimum value of drive current of a scan for a wet state of the aperture plate is determined as being indicative of end of dose. This may for example contribute to the trigger from the short scan of possible end of dose, and it may be the sole trigger event.

In another embodiment, the method comprises the step of the controller automatically stopping operation of the actuator upon detection of end of dose.

In a further aspect, the invention provides a non-transitory computer readable medium comprising software code to perform a method as defined in any embodiment when executing on a digital processor.

Additional Statements

According to the invention, there is provided a nebulizer comprising a vibrating aperture plate, a mounting, an actuator, and an aperture plate drive circuit having a controller, wherein the controller is configured to:

- measure an electrical drive parameter at each of a plurality of measuring points in a scan, each measuring point having a drive frequency; and based on the values of the parameter at the measuring points, make a determination of end of dose;
- wherein the controller is configured to determine a minimum value or a maximum value of the drive parameter in said scan and to execute an algorithm using said minimum or maximum value to calculate an indicator value for end-of-dose.

In one embodiment, the parameter is drive current and a minimum value of drive current during the scan is used for said algorithm.

In one embodiment, a minimum value of drive current which is approximately less than 30% of a minimum value of drive current of a scan for a wet state of the aperture plate is determined as being indicative of end of dose.

In one embodiment, the controller is configured to use said minimum value in combination with a value for maximum rate of change of said parameter during the scan.

In one embodiment, the controller is configured to utilize the ratio of maximum slope value and the minimum parameter value to provide an indicator.

In one embodiment, the controller is configured to multiply said indicator by a constant value.

In one embodiment, the controller is configured to perform the scan across a frequency range of 128 kHz and 165 kHz.

In one embodiment, the controller is configured to initiate the scan in response to a trigger of possible end of dose.

In one embodiment, the trigger is a short scan with a smaller number of measuring points and which detects a change of drive current above a threshold.

In one embodiment, the drive current threshold change is above 5 mA, and preferably about 8 mA.

According to another aspect, the invention provides a method of operation of a controller of a nebulizer comprising a vibrating aperture plate, a mounting, an actuator, and an aperture plate drive circuit, wherein the method comprises:

measuring an electrical drive parameter at each of a plurality of measuring points in a scan, each measuring point having a drive frequency;

based on the values of the parameter at the measuring points, making a determination of end of dose;

determining a minimum value or a maximum value of the drive parameter in said scan and executing an algorithm using said minimum or maximum value to calculate an indicator value for end-of-dose.

In one embodiment, the parameter is drive current and a minimum value of drive current during the scan is used for said algorithm.

In one embodiment, a minimum value of drive current which is approximately less than 30% of a minimum value of drive current of a scan for a wet state of the aperture plate is determined as being indicative of end of dose.

In one embodiment, the controller uses said minimum value in combination with a value for maximum rate of change of said parameter during the scan.

In one embodiment, the controller utilizes the ratio of maximum slope value and the minimum parameter value to provide an indicator.

In one embodiment, the controller multiplies said indicator by a constant value.

In one embodiment, the controller performs the scan across a frequency range of 128 kHz and 165 kHz.

In one embodiment, the controller initiates the scan in response to a trigger of possible end of dose.

In one embodiment, the trigger is a short scan with a smaller number of measuring points and which detects a change of drive current above a threshold.

In one embodiment, the drive current threshold change is above 5 mA, and preferably about 8 mA.

In another aspect, the invention provides a non-transitory computer readable medium comprising software code to perform a method as defined above in any embodiment when executing on a digital processor.

DETAILED DESCRIPTION OF THE INVENTION

Brief Description of the Drawings

The invention will be more clearly understood from the following description of some embodiments thereof, given by way of example only with reference to the accompanying drawings in which:—

DESCRIPTION OF THE EMBODIMENTS

Figure 6:
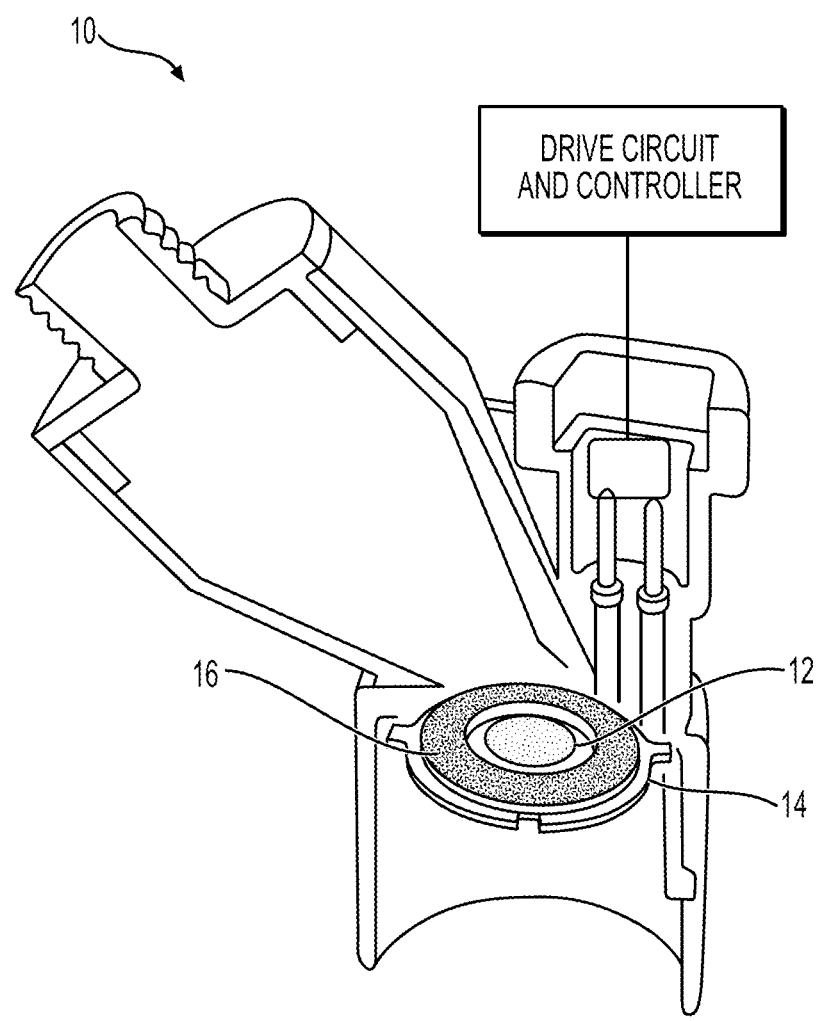
FIG. 6 is a diagram of an exemplary prior art nebulizer and drive circuit.

As shown in FIG. 6, a nebulizer 10 of the invention has a vibrating aperture plate 12, a mounting 14 for the plate 12, an actuator 16 such as a piezoelectric element, and an aperture plate drive circuit having a controller with a digital processor. The digital processor is programmed to drive the aperture plate so that liquid medication is aerosolized. It predicts when the liquid medication has been consumed, with the plate becoming dry. This is referred to as "end-of-dose (EOD)".

Figure 1:
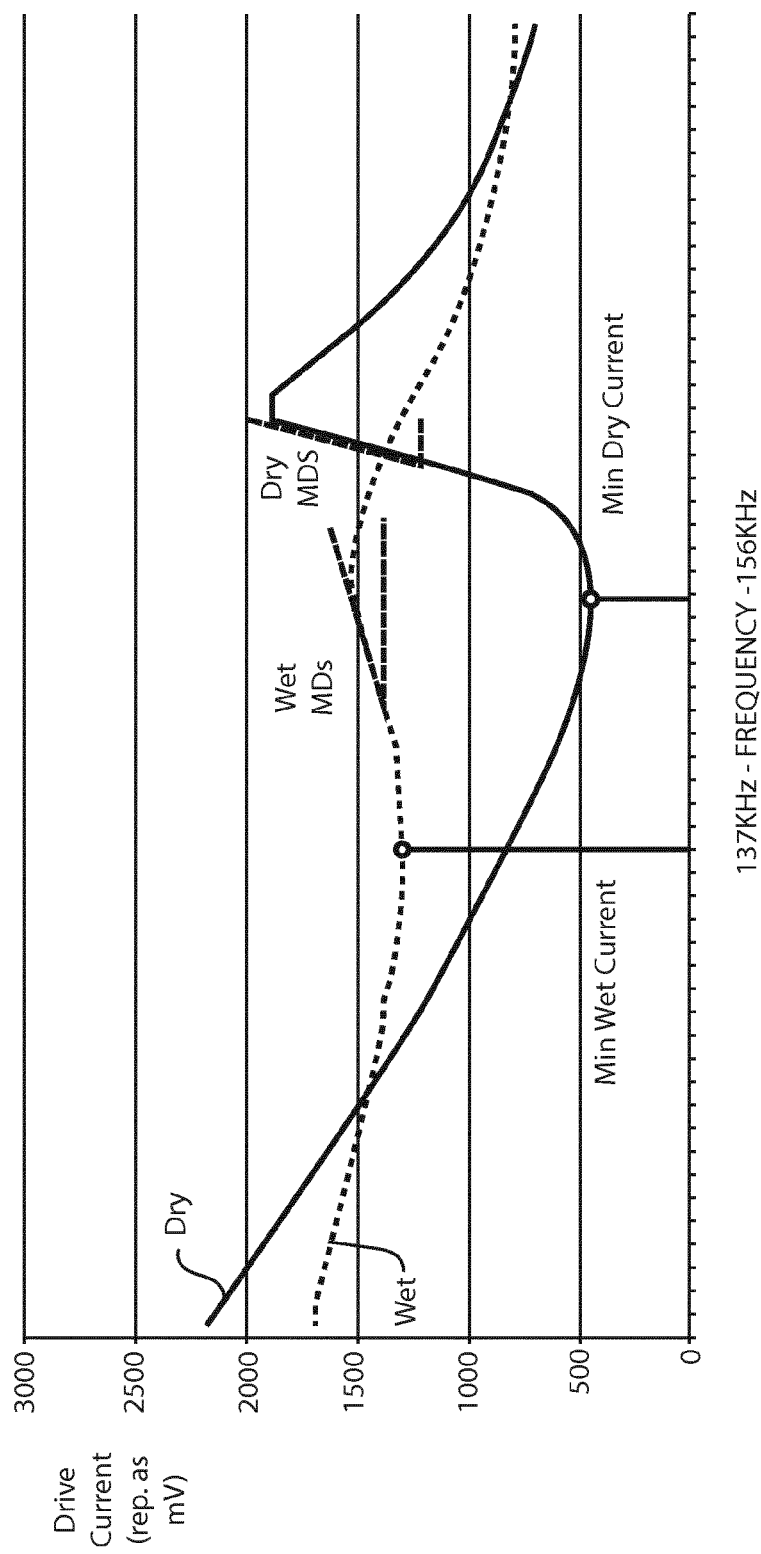
FIG. 1 is a plot of drive current versus frequency for wet and dry aperture plate states.

Referring to FIG. 1 plots for change of drive current with drive frequency for wet (dotted line) and dry (full line) states are illustrated for full scans which are triggered by change of state short scans in a manner as described in WO2015/010809. The full scan has many measuring points each with a specific drive frequency in the range of 137 kHz and 156 kHz in this embodiment. This is triggered in response to a short scan identifying a change in drive current.

However, in other embodiments there may not be a preceding short scan. For example, the full scan may be initiated in response to any other configured trigger, such as elapse of a pre-set time or a user input.

For aperture plate drive current measurement, the processor measures a voltage across a fixed shunt resistor. This provides enough information to determine the impedance of the nebulizer. This is essentially a current measurement.

When operating close to anti-resonance more current is consumed nebulizing in the wet state than in the dry state. During the scan of drive current values across multiple frequencies the minimum drive current is identified and the current consumption for this point is recorded.

The slope differential is also determined during the scan. The drive current (or "current consumption") at each measuring point is compared to the current drawn at the previous measuring point. The software routine executed by the processor records the maximum differential slope ("MDS") of drive current measurements found across the full frequency range.

As more power is necessary to drive the aperture plate in its wet state, the presence of liquid on the plate results in a higher current than the dry state. In addition to this, the presence of liquid has a dampening effect, resulting in a small rate of change of current across the frequencies in the wet state. On the other hand, in the dry state the MDS differential is a large value. These attributes are illustrated in the plots of FIG. 1.

Following the wet state plot of FIG. 1 it is seen that the maximum positive slope ("Wet MDS") is small and current at the anti-resonant point in the wet state is much higher than when in the dry state. Typically, the MDS for the wet state is in the range of 10° to 54°.

On the other hand, for the dry state plot the current dips to a minimum which is only about 30% of that for the wet state. Also, the maximum slope ("Dry MDS") is much higher, by a factor of about 4 when compared to the wet state maximum slope.

It has been found that a particularly reliable and accurate end-of-dose determination can be made by employing both the scan's minimum current and MDS during the scan. In one embodiment the algorithm is:

EOD_Value=(max·slope/min·*I*)*1000 where, max·slope is the scan's maximum slope value, 1000 is a fixed number to scale the value and being selected for ease of computations, and to allow use of low-cost processor, and min·I is drive current at the anti-resonant point, which is the preceding minimum.

Figure 2:
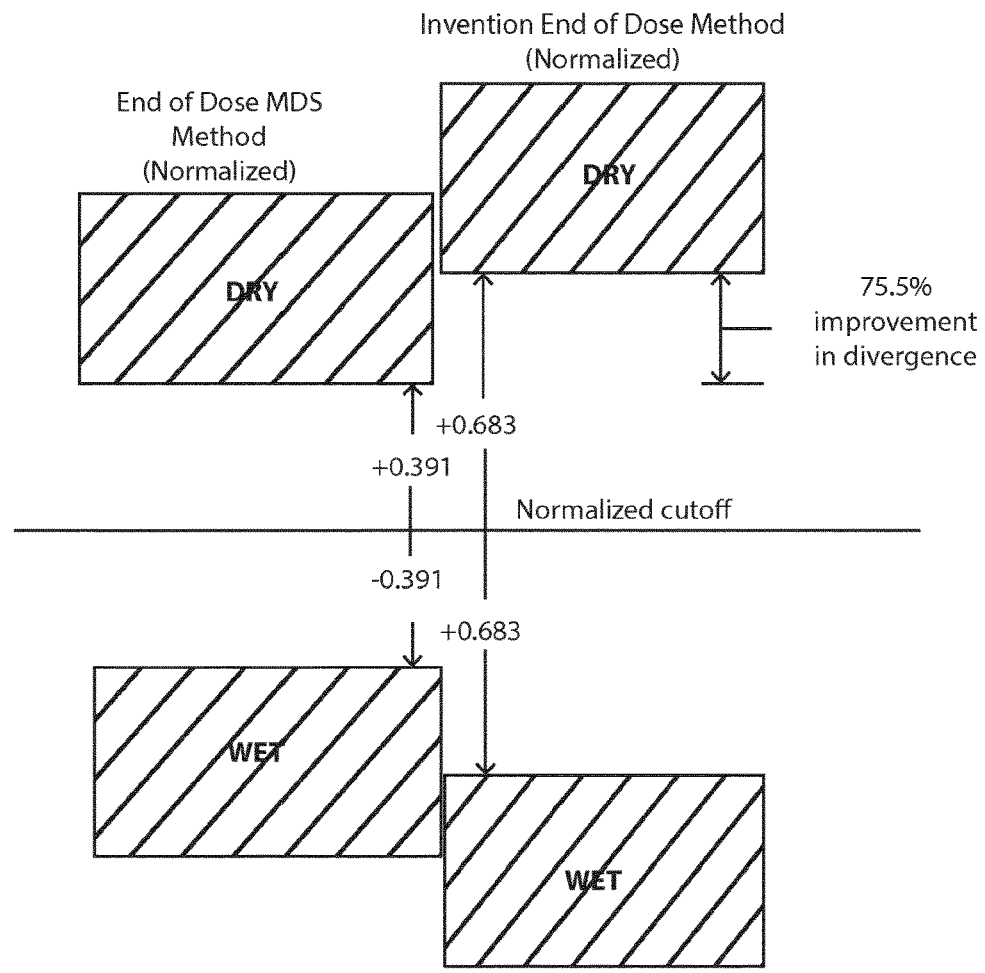
FIG. 2 is a diagram illustrating improvement of the invention in identification of a dry state.

As shown in FIG. 2 there is a 75% improvement in divergence between dry and wet, as compared to the prior art approach in which only MDS is employed. This arises from employing the preceding current minimum value according to this algorithm.

Figure 3:
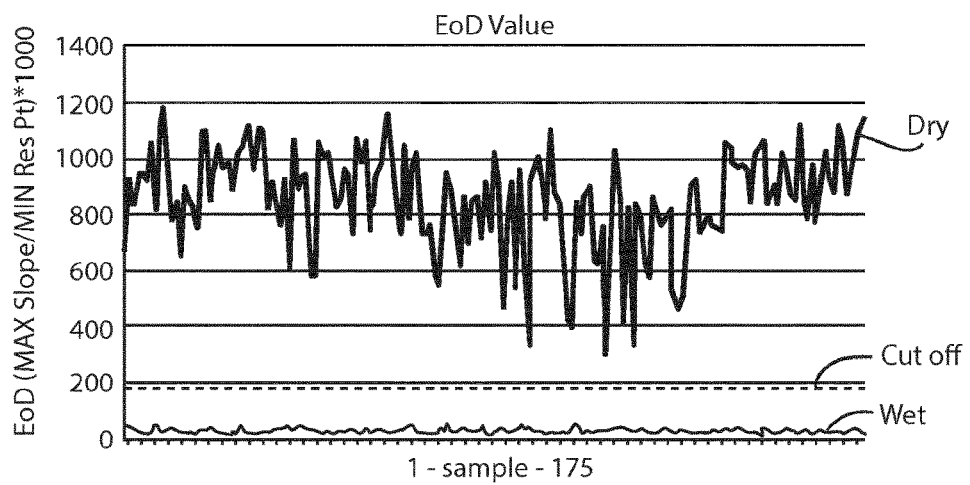
FIG. 3 is a set of plots of values of a dry plate indicator value, a cut off or threshold fixed value, and wet plate values, versus sample number.

FIG. 3 shows examples of the values. As is clear from this plot, the values for the dry state are very well above the threshold, and so there is very accurate and prompt identification of the dry state.

Figure 4:
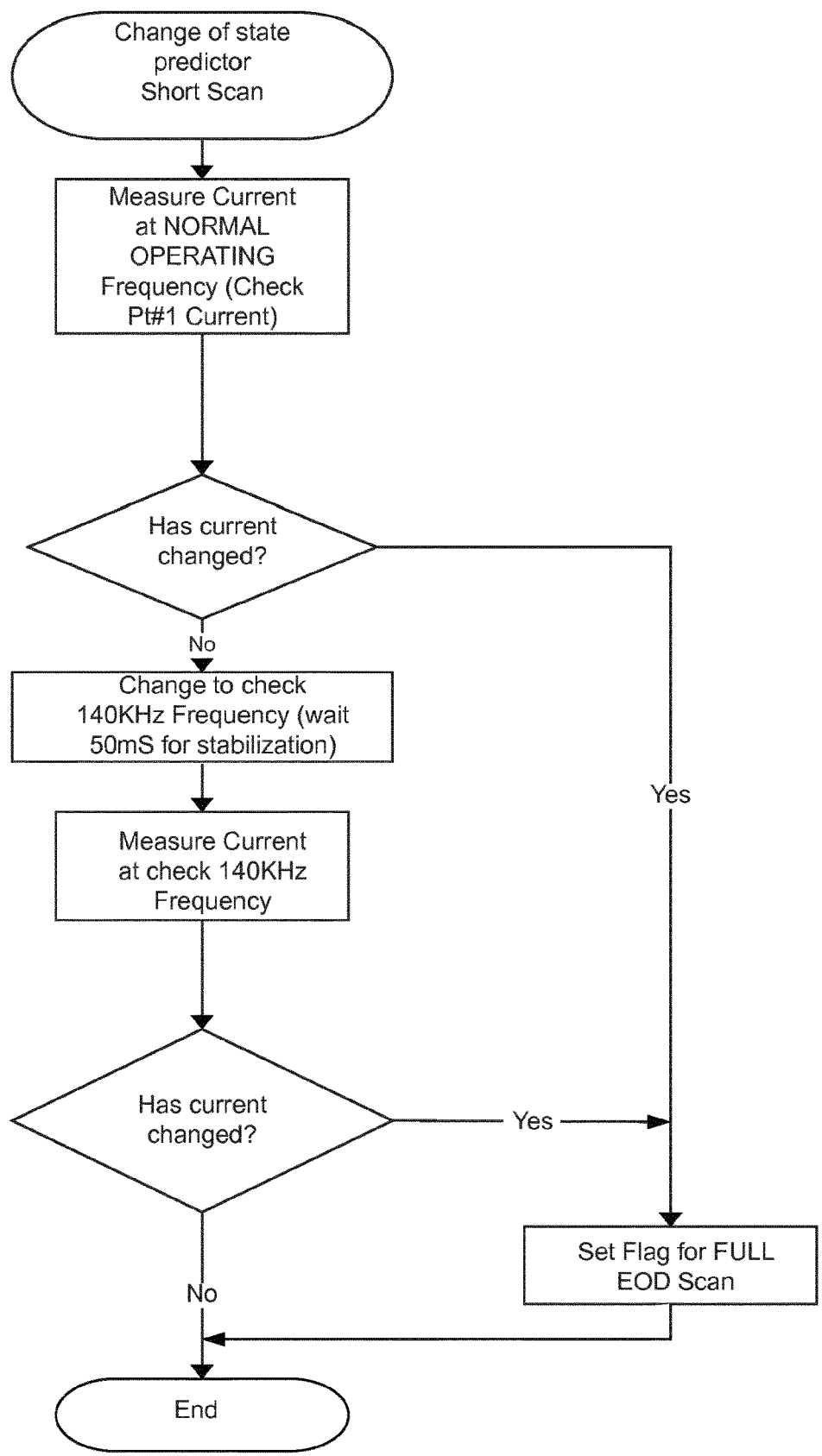
FIGS. 4 and 5 are flow diagrams for operation of a nebulizer controller to predict end of dose, FIG. 4 showing a change of state predictor short scan and FIG. 5 showing a full scan for full analysis of potential end of dose.
Figure 5:
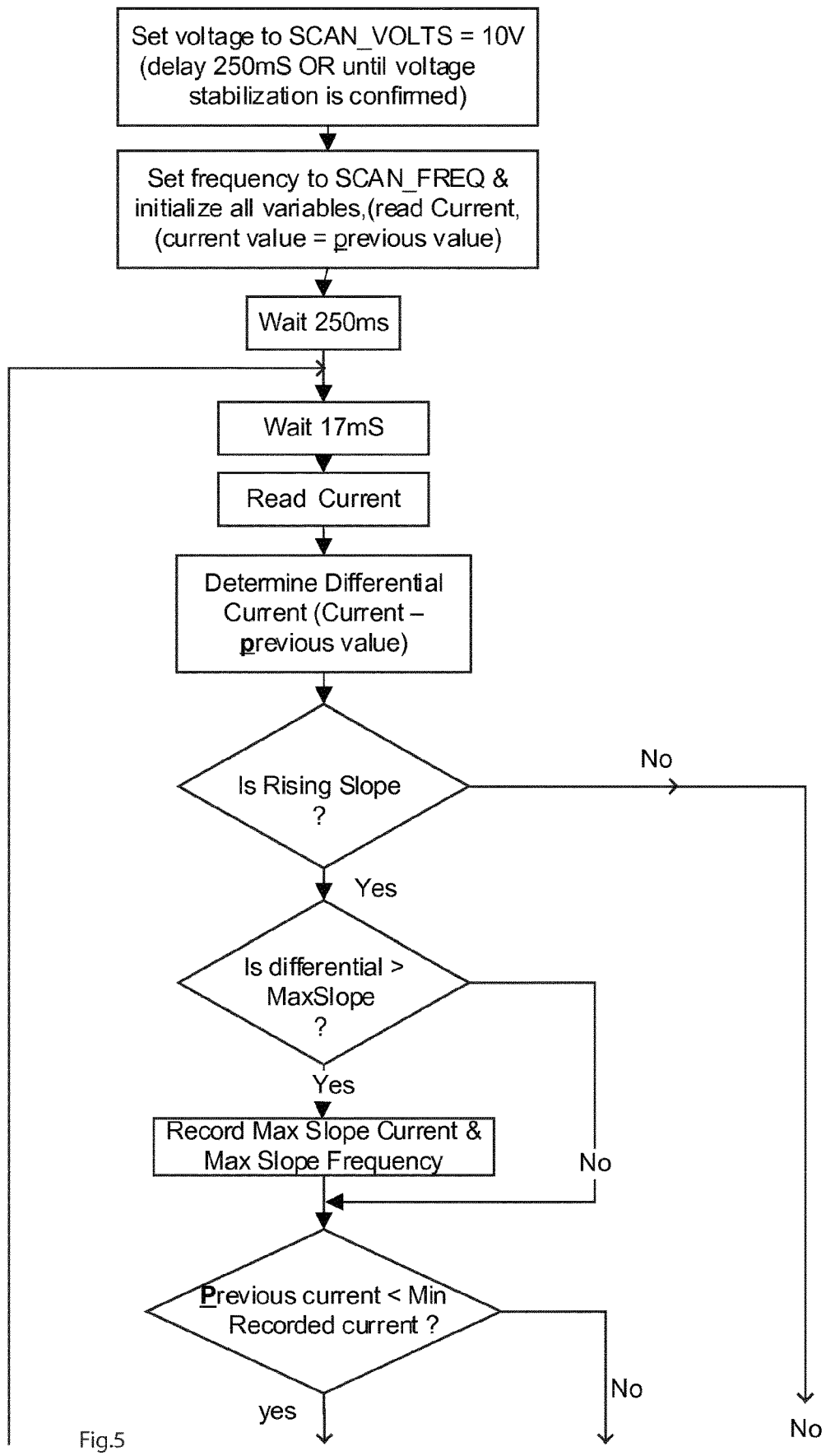
Figure 5:
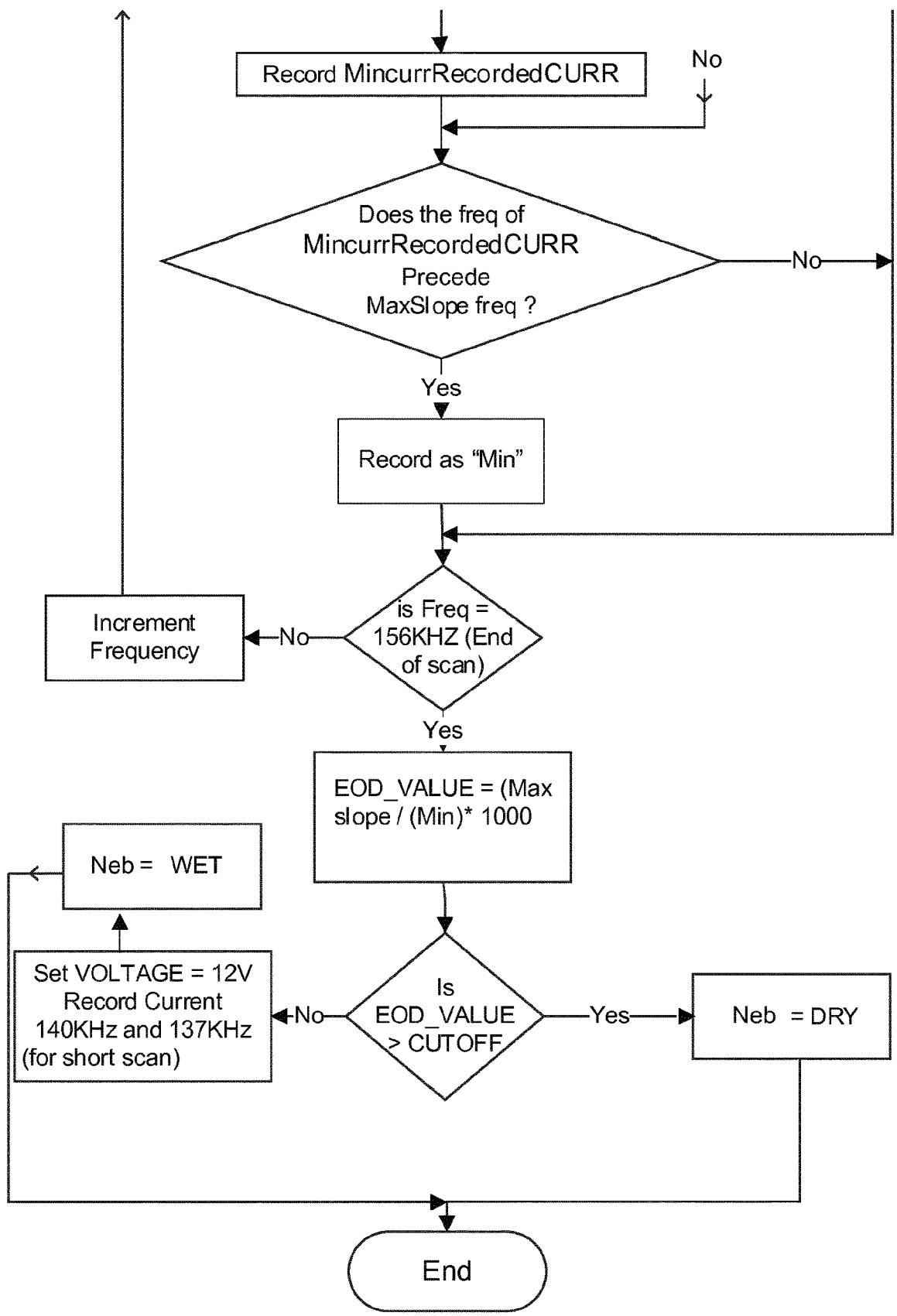

The full EOD algorithm (FIG. 5) is executed by a digital processor of the nebulizer controller upon a trigger provided by a short scan, shown in FIG. 4. The short scan is a predictor of potential end of dose. It identifies changes of current at the measuring points, and if the current at either of these two points has changed by greater than 8 mA this routine will flag a possible change of state of the aperture plate and call for a full scan to confirm the change of state. The short scan method monitors the current consumption at two different frequencies of operation.

1. 137 KHz/128 KHz (Operating Frequency)
2. 140 KHz ($2^{nd}$ frequency where nebulization is not interrupted)

Referring to FIG. 5:

The minimum current point relates to the minimum point preceding the MDS (as shown in FIG. 1) and is referred to as the anti-resonant current.

The EOD_value formula contains a multiplier of 1000, this is an arbitrary value chosen to simplify the microprocessor calculations.

When a wet state is identified, the EOD routine sets the operating voltage and then records the current consumption at the two check points which is then used by short scan (FIG. 4) method as the reference current.

Configuration Parameters

SCAN_FREQ (frequency values for each measuring point) 137 KHz to 156 KHz

OPERATING_FREQ 137 KHz

SCAN_VOLTS 10V

RUN_VOLTS 12V

EOD_CUTOFF 174

The EOD_CUTOFF value was determined from a sample size of 175 pieces, it was chosen as the mid-point between the max wet and the min dry values. Please refer to FIG. 3.

The addition of utilizing the minimum currents in the calculation of an EOD_value provides a more robust method of determining the wet/dry state of the nebulizer. These minimum currents correspond to the anti-resonant frequency of the aperture plate, and this anti-resonant frequency may differ from the wet to dry state, due to the presence of liquid on the aperture plate Also, the anti-resonance current when the aperture plate is wet will be higher than the anti-resonance current when it is dry as additional energy is required to displace the liquid in the wet state, which in turn translates to an additional electrical power requirement.

In summary, the main function of full end-of-dose scan is to determine the status of the plate. The scan finds the maximum rate of change in current found between successive frequencies (maximum slope). Another function is to determine the minimum current, that drawn at anti-resonance. The ratio of the max·slope/min·current is used to determine the status of the plate. This value is much greater when the plate is dry than when it is wet, with a much greater differential than when only using the slope value.

When a direct comparison to the prior end-of-dose method described in WO2015/010809 is made, it can be seen that the method of the invention has greater than 75% improved divergence between the wet and dry groupings, as shown in FIG. 2.

By providing significantly more accurate and reliable indications of end of dose, the invention helps to achieve a longer useful lifetime of an aperture plate.

Also, the invention helps to provide a nebulizer which caters much better with variation of parameters associated within large scale manufacture. Despite excellent manufacturing practice, small variations in parameters exist within all the stages of manufacture, and when these variations are combined, they can lead to considerable differences in the operating parameters of a nebulizer. The extent of divergence in the calculated values between wet and dry states, ensures that EOD detection accuracy will be achieved every time.

Also, in the case, of over-moulded nebulizers, the complete vibratory actuator, including the piezo-electric element, is encapsulated (as shown in FIG. 6) to allow easier cleaning of the nebulizer after use. This however causes a restriction of movement, which significantly reduces the capability of the processor to identify the presence of liquid on the aperture plate. The invention circumvents this restraint due to its extent of sensitivity to the aperture plate becoming dry.

Nebulizers of the invention also provide several therapeutic benefits for patients such as those suffering from Cystic Fibrosis ("CF"), who need to spend long periods taking medication, often every day. Nebulizers for this application are typically over-moulded, and because the processor according to the invention provides instantaneous feedback on dose completion which, in the case of children, means less dosing time and also much less monitoring/assistance requirements from parents. This is especially so if the controller is configured to shut down the nebulizer and so extend the life of the nebulizer aperture plate. Also, by shutting off at the end of the delivery of medication, as identified by the end of dose, the nebulizer will dramatically improve the capability of battery powered devices to deliver longer periods on a single charge/set of batteries.

The invention is not limited to the embodiments described but may be varied in construction and detail. As an alternative to directly measuring drive current at each of the measuring points, it is envisaged that it may be indirectly measured by for example measuring impedance of the aperture plate. In this specification, where it is stated that drive current is measured, this may be either directly or indirectly. The frequency range may be within a different range, but is preferably within 128 kHz and 165 kHz, and more preferably about 137 kHz and 156 kHz.

The invention claimed is:

1. A nebulizer, comprising:
 a vibrating aperture plate;
 an actuator; and
 an aperture plate drive circuit having a controller, wherein the controller is configured to:
  measure drive current to the aperture plate;
  detect end-of-dose based on a minimum value of the drive current and a maximum rate of change of the drive current; and
  upon detection of end-of-dose, automatically stop operation of the actuator, and
  wherein the controller is further configured to detect the end-of-dose based on a ratio of the maximum rate of change and the minimum value of the drive current.

2. The nebulizer of claim 1, wherein the controller is configured to measure the drive current during a scan across a plurality of drive frequencies.

3. The nebulizer of claim 2, wherein the plurality of drive frequencies includes a drive frequency range of 128 kHz to 165 kHz.

4. The nebulizer of claim 2, wherein the controller is configured to initiate the scan in response to a trigger of possible end-of-dose.

5. The nebulizer of claim 4, wherein the trigger is a short scan with a smaller number of measuring points and which detects a change of drive current above a threshold.

6. The nebulizer of claim 5, wherein the threshold is above 5 mA.

7. The nebulizer of claim 1, wherein the minimum value of the drive current for end-of-dose corresponds to approximately less than 30% of a minimum value of the drive current for a wet state of the aperture plate.

8. A method of operation of a controller of a nebulizer comprising a vibrating aperture plate, an actuator, and an aperture plate drive circuit, the method comprising:
 measuring drive current to the aperture plate at multiple discrete measuring points, each measuring point associated with a particular drive frequency;
 detecting end-of-dose based on a ratio of a maximum rate of change of the drive current and a minimum value of the drive current; and
 upon detection of end-of-dose, automatically stopping operation of the actuator.

9. The method of claim 8, wherein the plurality of drive frequencies includes a drive frequency range of 128 kHz to 165 kHz.

10. The method of claim 8, further comprising initiating a scan in response to a trigger of possible end-of-dose.

11. The method of claim 10, wherein the trigger is a short scan with a smaller number of measuring points and which detects a change of drive current above a threshold.

12. The method of claim 11, wherein the threshold is above 5 mA.

13. The method of claim 8, wherein the minimum value of the drive current for end-of-dose corresponds to approximately less than 30% of a minimum value of the drive current for a wet state of the aperture plate.

14. A non-transitory computer readable medium comprising software code to perform a method of operation of a controller of a nebulizer comprising a vibrating aperture plate, an actuator, and an aperture plate drive circuit, when executing on a digital processor, the method comprising:
 measuring drive current to the aperture plate at multiple discrete measuring points, each measuring point associated with a particular drive frequency;
 detecting end-of-dose based on a ratio of a maximum rate of change of the drive current and a minimum value of the drive current; and
 upon detection of end-of-dose, automatically stopping operation of the actuator.

* * *